United States Patent
Huber et al.

(10) Patent No.: US 12,369,786 B2
(45) Date of Patent: Jul. 29, 2025

(54) OPTICAL INSTRUMENT AND METHOD FOR PRODUCING AN OPTICAL DEVICE

(71) Applicant: KARL STORZ SE & Co. KG, Tuttlingen (DE)

(72) Inventors: Christian Huber, Tuttlingen (DE); Dieter Hüls, Tuttlingen (DE); Mario Sterk, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 910 days.

(21) Appl. No.: 17/462,843

(22) Filed: Aug. 31, 2021

(65) Prior Publication Data
US 2022/0061649 A1 Mar. 3, 2022

(30) Foreign Application Priority Data
Sep. 1, 2020 (DE) .................. 10 2020 122 846.5

(51) Int. Cl.
*A61B 1/00* (2006.01)
*A61B 1/06* (2006.01)
*A61B 1/267* (2006.01)

(52) U.S. Cl.
CPC ............ *A61B 1/267* (2013.01); *A61B 1/0011* (2013.01); *A61B 1/0676* (2013.01)

(58) Field of Classification Search
None
See application file for complete search history.

(56) References Cited

U.S. PATENT DOCUMENTS

| 4,901,708 A * | 2/1990 | Lee .................. A61B 1/07 600/199 |
| 2003/0233024 A1 | 12/2003 | Ando |
| 2005/0089286 A1* | 4/2005 | Hatori .............. A61B 1/012 385/117 |
| 2008/0208006 A1 | 8/2008 | Farr |
| 2009/0173875 A1 | 7/2009 | Ichimura et al. |

(Continued)

FOREIGN PATENT DOCUMENTS

| CN | 203914844 U | 11/2014 |
| DE | 102013007491 A1 | 10/2014 |

(Continued)

OTHER PUBLICATIONS

Machine english translation for Iwasak WO 2014/111990 (Year: 2014).*

(Continued)

*Primary Examiner* — Jan Christopher L Merene
(74) *Attorney, Agent, or Firm* — Jason H. Vick; Amped IP LLC (57) ABSTRACT

An optical instrument for viewing living things for medical purposes comprises an instrument body (20, 30, 40, 50, 60), wherein the instrument body (20, 30, 40, 50, 60) accommodates at least one optical element (21, 31, 41, 51, 61) for receiving light from a region outside the instrument body (20, 30, 40, 50, 60) and at least one illumination unit (22, 23, 32, 42, 52*a*, 52*b*, 62) for illuminating this region. The optical element (21, 31, 41, 51, 61) is held in the instrument by a mount (25, 33, 43, 53, 63) whose distal edge extends beyond the optical element (21, 31, 41, 51, 61) and is reshaped in at least one portion in order to hold the optical element (21, 31, 41, 51, 61). Non-reshaped portions (27, 35, 45, 55*a*, 55*b*, 65) of the distal edge serve as a stray-light protection, which keeps illumination light away from the optical element (21, 31, 41, 51, 61). A method (70) for producing such an instrument is also proposed.

8 Claims, 5 Drawing Sheets

(56) References Cited

U.S. PATENT DOCUMENTS

| | | |
|---|---|---|
| 2011/0077465 A1 | 3/2011 | Mizuyoshi et al. |
| 2014/0107422 A1 | 4/2014 | Huels et al. |
| 2017/0135566 A1* | 5/2017 | Gerrans ............. A61B 5/14551 |
| 2018/0168433 A1 | 6/2018 | Meyer et al. |
| 2019/0159660 A1 | 5/2019 | Maichle et al. |
| 2020/0060520 A1* | 2/2020 | Sørensen ............. A61B 1/0676 |
| 2021/0369087 A1 | 12/2021 | Kodama et al. |

FOREIGN PATENT DOCUMENTS

| | | | |
|---|---|---|---|
| DE | 102017127827 A1 | 5/2019 | |
| EP | 2491848 A1 * | 8/2012 | ........... A61B 1/0008 |
| EP | 3613326 A1 | 2/2020 | |
| EP | 3613332 A1 | 2/2020 | |
| JP | 2004-016410 A | 1/2004 | |
| WO | WO 2013/031276 A1 | 3/2013 | |
| WO | WO 2014/111990 A1 | 7/2014 | |
| WO | WO 2020/188685 A1 | 9/2020 | |

OTHER PUBLICATIONS

European Search Report for corresponding European Application No. 21192993.0, mailed Jan. 18, 2022.

Office Action for German Patent Application No. 102020122846.5, mailed Jul. 1, 2021.

* cited by examiner

OPTICAL INSTRUMENT AND METHOD FOR PRODUCING AN OPTICAL DEVICE

CROSS-REFERENCE TO RELATED APPLICATIONS

This application claims the benefit under 35 U.S.C. 119 (a) to German Patent Application No. 10 2020 122 846.5, filed 1 Sep. 2020, the disclosure of which is incorporated herein by reference in its entirety.

The present invention relates to an optical instrument for viewing living things for medical purposes.

Such instruments are often designed as endoscopes for looking into the body, as microscopes or exoscopes for viewing the body from outside the body, or as laryngoscopes for use in intubation.

Nowadays, endoscopes find use in many applications in medicine and technology. An endoscope typically comprises a rigid, semi-rigid or flexible elongate shaft, which is suitable for insertion into a cavity. In most cases, an endoscope objective for producing an image of an object field in the cavity is arranged in the distal end region of the shaft (i.e. the end region remote from the observer). The endoscopic image can be transmitted to the proximal end of the endoscope (the end near the observer) by way of optical or electronic means that are arranged in the interior of the shaft, said endoscopic image being made available at said proximal end for observation by a user or for display.

Since there is generally not enough light within the cavity observed, an illumination light guide is often also arranged inside the shaft in order to transport illumination light to the distal end of the endoscope, where it is used to illuminate the cavity. To introduce the illumination light into the endoscope, a port for attachment of a fiber-optic cable is often present near the proximal end, with which cable the illumination light can be supplied from a separate light source.

Alternatively or in addition, light can also be made available via illumination means arranged distally on the shaft, for example LEDs or laser diodes.

In the case of modern video endoscopes, one or more image sensors for capturing an image produced by the objective are frequently arranged at the distal end. Alternatively, the image sensors can also be arranged at the proximal end of the endoscope, for example in a handle or in a camera head.

Laryngoscopes can be similarly configured and, instead of a shaft, in most cases have a blade and a handle. The objective, or also the image sensor for capturing images of the larynx, is in most cases mounted on the blade, likewise the illumination means. Laryngoscopes are used to safely introduce intubation tubes into the trachea of patients.

Objectives and image sensors are in most cases closed at the distal end by a window, a lens or another optical element, in order to protect the optical system and to be able to design the instruments sealingly, such that they are suitable for intensive cleaning by chemicals, high temperatures, steam, and high pressures.

Microscopes and exoscopes are used to view the body from the outside and likewise provide optical elements and cameras, likewise illumination means. They are often fastened to stands or retaining arms and allow the outer surface of the body or the inner organs to be viewed through a suitable natural or artificial opening. Microscopes and exoscopes are often able to provide a greatly enlarged image of the observed region by using suitable optics and digital zoom functions.

A common feature of all the instruments is that optical means for receiving light and also illumination means have to be provided in a distal region of the instruments, i.e. at an end directed toward the patient. On account of the spatial proximity of these components to one another, there is often the problem of light emerging undesirably from an illumination means and then straying into the optical system of the instrument either directly or through other parts of the instrument. This adversely affects the image quality, since this stray light superposes the light that is reflected from the observation region and that is actually used to generate the images, and it thus adversely affects the generated image. The smaller the region of the instrument in question in which optical means and illumination units are arranged close to one another, the more difficult it is to keep the stray light away from the optical system of the instrument. Particularly in the field of endoscopes and laryngoscopes, the distal end often has an end face of only a few millimeters in which all the components are arranged, in some cases with additional working channel inlets or means for irrigation and suction, which likewise take up space.

DE 10 2013 007 491 A1 discloses a stray-light stop for medical optical instruments, which is fitted externally onto the shaft of the instrument. This stop is suitable for ensuring that stray light from light sources located away from the distal end of the instrument is kept away from the optical system of the instrument. However, the stop takes up a great deal of space and changes the dimensions of the instrument, and it is not suitable for the mutual separation of optics and illumination means that are arranged close to one another.

EP 2 491 848 A1 describes a video endoscope having a distal end in which windows are integrated for image capture and for illumination. The illumination windows are arranged in depressions, while the image capture window is mounted in a projection with a beveled edge. A disadvantage is that the distal end face for this arrangement must be of a very complex design.

US 2011/0 077 465 A1 discloses various arrangements of light source and optical system for image capture at the distal end of a video endoscope.

CN 2 03 914 844 U describes an arrangement for preventing stray light on an endoscope, in which arrangement the optical system and the illumination units are covered with a specially designed cover glass.

US 2008/0 208 006 A1 discloses a video laryngoscope in which a distal optical element is surrounded all the way round by a mount. LEDs arranged alongside are set back in relation to the frontmost optical face.

EP 3 613 326 A1 discloses a video endoscope which is covered distally with a window. Two projections extending proximally between the optical system of the instrument and the illumination units are integrated laterally in the window in order to keep stray light away.

JP 2004-016 410 A describes covering the distal end of an endoscope with a three-part lens, wherein the central part covers the optical system and the lateral parts cover the illumination means. Protective plates, which prevent admission of stray light into the optical system, are adhesively bonded in between the parts of the lens.

EP 3 613 332 A1 describes a distal part of an endoscope with a camera and an illumination means, wherein a stray-light protection is arranged in the distal end face between the illumination means and the camera.

A disadvantage of these solutions known from the prior art is that they in each case constitute solutions for screening of stray light that are difficult to produce and that moreover require additional space.

It is therefore an object to make available an instrument having a stray-light protection between an illumination means and an optical element of the instrument, which stray-light protection is able to be realized on a small surface area and does not itself adversely affect the image capture. A further object of the invention is to make available a method by which an instrument with a stray-light protection of this kind can be produced as easily as possible.

These objects are achieved by a device according to the claims appended hereto.

Advantageous developments of the invention are set forth in the dependent claims.

An optical instrument of the kind described here is suitable for viewing a living thing for medical purposes. For example, it can be an endoscope, a microscope/exoscope or a laryngoscope, as used for diagnosis and treatment in humans and animals.

The instrument has an instrument body, wherein the instrument body accommodates at least one optical element for receiving light from a region outside the instrument body and at least one illumination unit for illuminating this region. The optical element is held in the instrument by a mount which extends in the distal direction beyond the optical element and there forms a distal edge. The distal edge is reshaped in at least one portion such that the reshaped portion of the distal edge holds the optical element in the distal direction with form-fit engagement. The shape of the distal edge in this portion or in these portions is therefore such that the distal edge holds the optical element in the distal direction with form-fit engagement. At least one non-reshaped portion of the distal edge is arranged such that it forms a stray-light protection, by which illumination light coming from the illumination unit is kept away from the optical element. A non-reshaped portion of the distal edge is in the present case a portion of the distal edge that does not help or is not designed to hold and secure the optical element. The shape of the distal edge in the region of the non-reshaped portion or of the non-reshaped portions is therefore such that it does not hold the optical element in the distal direction by form-fit engagement.

In the instrument body, or in a separate camera, the instrument can moreover have one or more image sensors for capturing images and videos. The optical element is, for example, part of an objective for image capture, a prism or also a window or cover glass, e.g. in the manner of a plane-parallel plate. It can be round and, for example, made of glass or plastic. The optical element is held by a mount, for example in the form of a cylinder with a circular cross section which is part of the instrument or is arranged in the instrument. The mount can be made of metal. The mount can directly surround the optical element such that the distal edge directly borders the optical element. A reshaped portion of the distal edge can be a part, in particular a flat part, of the distal edge that extends in a direction perpendicular or approximately perpendicular to the longitudinal axis of the mount and parallel to the optical element. The optical element, at its distal face, is partially covered and held in its outer edge region by the reshaped portion of the distal edge of the mount. A non-reshaped portion of the distal edge can be a substantially straight part of the distal edge that extends distally beyond the optical element, in the direction of extent of the mount, and there forms a stray-light protection.

Optical elements of this kind are usually clamped or adhesively bonded or their edge is metal-coated at the circumference and the element is soldered into the mount. Since medical instruments have to undergo intensive cleaning in cleaning liquid or in autoclaves, they have to be produced in such a way that they are sealed from the outside. Unfortunately, a frequent problem is that, as a consequence of incorrect handling or cleaning or due to other circumstances, an adhesive for example, which holds the optical element in the mount, is washed out. The adhesive is therefore unintentionally removed and the optical element can therefore fall out of the mount during the use of the instrument. It is therefore a feature of the instrument described here that the mount is designed in such a way, and the optical element is arranged in the mount in such a way, that the mount protrudes distally, i.e. out of the instrument and in the direction of the patient, and there forms a distal edge around the element. The distal edge is reshaped in at least one subportion of the distal edge, such that it engages around the optical element partially with form-fit engagement and additionally secures and holds the latter distally. Here, portion is intended to signify a portion of the circumference of the distal edge. In this way, the element cannot fall out of the mount even if an adhesive or the like no longer secures the element.

The one or more illumination units are arranged together with the optical element in the instrument and, for example, illuminate an operating site, i.e. a spatial region located distally in front of the instrument, in particular the region from which light is received by the optical element and is supplied for imaging. The illumination unit can be an LED (light emitting diode), a laser diode or a conventional lighting means such as a light bulb. However, it can also be composed of the fiber ends of a fiber optic, the attached light source of which is located at another site in or outside the instrument. The illumination can be in a single color or multi-colored or white and, for example, may be suitable for fluorescence excitation. It is also known to generate white light by using a laser to excite a so-called phosphor arranged in the instrument.

LEDs are small but planar illumination means which, in medical instruments, are often fitted behind a window and a transparent sealing compound. It can happen that not only the LED surface but also the surface of the sealing compound scatters and emits light. Where an illumination unit is referred to in the present text, it can therefore also signify this entire light-emitting surface. The surface of the LED is sometimes also equivalent to the light-emitting surface. If appropriate, an optical element such as a lens can be part of the illumination unit, which shapes the illumination light and helps to illuminate defined regions.

In medical instruments, particularly those used in minimally invasive medicine, there is often only very little space available for illumination, optics and further components, often only a few millimeters. Even small illumination units such as LEDs can have a large illumination surface relative to their thickness or height, i.e. their space requirement in the distal direction away from the surface. At the same time, the illumination and optics and imaging means in the instrument surface should be arranged for example in one plane so that they do not block or shade one another. For example, the optical element and the illumination unit or the illumination units are arranged in a distal end face of the instrument. The optical element is the farthest distal optical element of the instrument. It is therefore easily possible that direct light or stray light from the illumination units enters the optics and thereby adversely affects the image quality. Where stray light is referred to in this text, this is therefore also intended to signify incident light direct from the illumination unit, and vice versa.

In the case of the present instrument, it has now been found that the stray-light incidence can be considerably reduced if the distal edge of the mount is not completely reshaped for holding the optical element. Instead, the distal edge is reshaped only in at least one portion that is sufficient to hold the element. Otherwise, the distal edge remains as a stop or stray-light protection. The portion of the distal edge that is reshaped is suitably chosen such that the non-reshaped part is suitable as a stray-light protection. This is described in greater detail below.

So as not to adversely affect the function of the optical element, the reshaped portion of the distal edge should be as small as possible. At the same time, production of the instrument should be made easier. The reshaping can therefore be effected by bending, for example. In the case of a material such as plastic, the edge can also undergo hot or thermoplastic deformation.

In particular, it is proposed here that the mount be made of metal. It is further proposed that the one or more portions of the distal edge be mechanically reshaped by caulking. This is done, for example, using a suitable stamping tool. The distal edge can undergo cold or hot caulking. Caulking permits safe deformation of even very small edges, with dimensions of less than one millimeter. The optical element is then held in the mount by the caulked portion or the caulked portions of the distal edge.

To ensure that the remaining, non-reshaped part of the distal edge forms sufficient stray-light protection and that the optics are not adversely affected, the height of the distal edge of the mount, which protrudes distally beyond the optical element, is preferably at least 0.5% and at most 5% of the circumference of the distal edge.

Particularly in the case of minimally invasive instruments having a small diameter, this can mean that the non-reshaped or caulked distal edge has very small dimensions. If the mount has for example a diameter of 1 millimeter, the distal edge in the one or more non-reshaped portions is preferably about 0.016 to 0.16 mm high. Since this also corresponds to the height of the distal edge prior to the reshaping, caulking is particularly suitable as a deformation method for these small dimensions.

It is alternatively conceivable that the height of the distal edge in the one or more non-reshaped portions measures up to 10% of the circumference of the distal edge of the mount.

The illumination unit moreover has a light-emitting face. The at least one non-reshaped portion is advantageously arranged such that it is located between the optical element and the light-emitting face. In this way, a direct line between illumination unit and optical element is interrupted by the non-reshaped portion and the optics are protected from stray light.

Provision is made in particular that the at least one non-reshaped portion of the distal edge comprises at least one part A of the circumference of the distal edge corresponding to an angle Amax, which is spanned by straight lines between the center point of the optical element and points of the boundary of the light-emitting face, in such a way that the angle is maximal.

If one imagines straight lines being drawn from a center point of the optical element to the outer boundary of the light-emitting face of the illumination unit, these straight lines form different angles to each other. If one considers the greatest angle that can be formed by these straight lines, this finally includes the illumination face, i.e. the light-emitting face, and the straight lines meet the outermost boundaries of the light-emitting face. Within this angle, a part A of the distal edge between the straight lines runs over a part of its circumference about the optical element. This part in the present case forms at least or precisely the non-reshaped portion of the distal edge, while the distal edge beyond this is reshaped, for example by caulking. In this way, the stray-light protection is set up precisely between the optical element and the illuminating face of the illumination unit.

Provision can further be made that the non-reshaped portion of the distal edge comprises at least a part B of the circumference of the distal edge between two points a and b, in such a way that the respective tangent, which touches the distal edge at these points, intersects or touches the light-emitting face and the length of the part B between a and b is maximal.

The part B thus runs between two points a and b on the distal edge where an imaginary tangent to the distal edge intersects or touches the light-emitting face of the illumination unit. This will be the case at the outermost limits of the light-emitting face, and the points a and b in this consideration lie a maximum distance apart from each other, such that they could still be impinged by illumination light. Therefore, the non-reshaped portion of the distal edge can comprise at least this part B, in order to provide particularly good protection against direct or stray light.

Alternatively, the non-reshaped portion of the distal edge can lie between these values, i.e. at least the part A and at most the part B according to the above definitions. The non-reshaped portion of the distal edge thus comprises at least part A and at most part B of the circumference between two points a and b, in such a way that the respective tangent that touches the distal edge at these points intersects or touches the light-emitting face, such that the length of the part B is maximal. As to which embodiment is the most suitable, a person skilled in the art will determine this on the basis of the specific instrument and, for example, the brightness of the illumination means, the properties of the optical element and the like.

The instrument described here is in particular a laryngoscope with a handle and with a blade, wherein the optical element and the illumination unit are arranged at the blade. Laryngoscopes are instruments for viewing the larynx during insertion of an intubation tube into the trachea. The blade serves as a lever in order to be able to open the patient's mouth and depress the tongue and insert the tube. Viewing is carried out via the optical element and the illumination unit on the blade, for example an objective with image sensor, which can be arranged together with one or more LEDs on the blade. The image captured by the image sensor is shown on a monitor. A video laryngoscope of this kind has to be cleaned after each use, for which reason secure fixing of the optical element is very important. At the same time, the imaging must not be adversely affected by stray light, since the intubation has to be performed quickly and correctly so as not to endanger the patient.

In one embodiment of the instrument, provision is made that the instrument has at least two illumination units, and the distal edge is reshaped in at least two separate portions, such that the non-reshaped portions keep illumination light from the two illumination units away from the optical element.

To obtain uniform illumination of a region viewed through the instrument, it is often necessary to have a plurality of illumination units, for example two. They can be arranged on both sides of the optical element. The distal edge of the mount is then designed and reshaped in two portions, such that these portions hold the optical element, while the remaining portions of the distal edge serve as stray-light protection and are suitably oriented to the two illumination units. For this purpose, the aforementioned features can all be used analogously in order to produce a particularly advantageous instrument. In particular, the edge can also have been caulked here for the reshaping.

A method for producing an optical instrument for viewing a living thing for medical purposes comprises the following steps:

providing an instrument body, arranging, in the instrument body, at least one optical element for receiving light from a region outside the instrument body and at least one illumination unit for illuminating this region, arranging the optical element in a mount, such that the mount extends in the distal direction beyond the optical element and there forms a distal edge, fastening the mount in the instrument body, and reshaping the distal edge in at least one portion, such that the reshaped portion of the distal edge holds the optical element in the distal direction with form-fit engagement, and the at least one non-reshaped portion of the distal edge is arranged such that it forms a stray-light protection by which illumination light coming from the illumination unit is kept away from the optical element.

In the case where the instrument is intended to have more than one illumination unit, the method can further comprise the following steps:

arranging at least a second illumination unit in the instrument body and reshaping a second, separate portion of the distal edge, such that the non-reshaped portions of the distal edge keep illumination light, coming from the two illumination units, away from the optical element.

The step of reshaping can in particular comprise caulking portions of the distal edge.

The steps of said method can be carried out in another order than the one given here, and further production steps can be provided that are not part of the present invention. In particular, in the region of the distal edge, the mount can first of all be reshaped, in particular caulked, in one or more portions by a device configured for this purpose. Thereafter, the optical element can be arranged in the mount from the proximal direction, and the mount can be arranged in the instrument body. In this way, the optical element cannot be damaged during the reshaping.

The different embodiments and features of the instrument that have been mentioned above can also all be features of the method set forth here.

The invention also comprises an optical instrument for viewing a living thing for medical purposes, which optical instrument has been produced by the method described above.

The optical instrument can have all of the features, individually or in combination, as have already been described above for an optical instrument.

Further aspects of the invention will become clear from the following description of preferred illustrative embodiments and from the accompanying drawings, in which.

Figure 1:
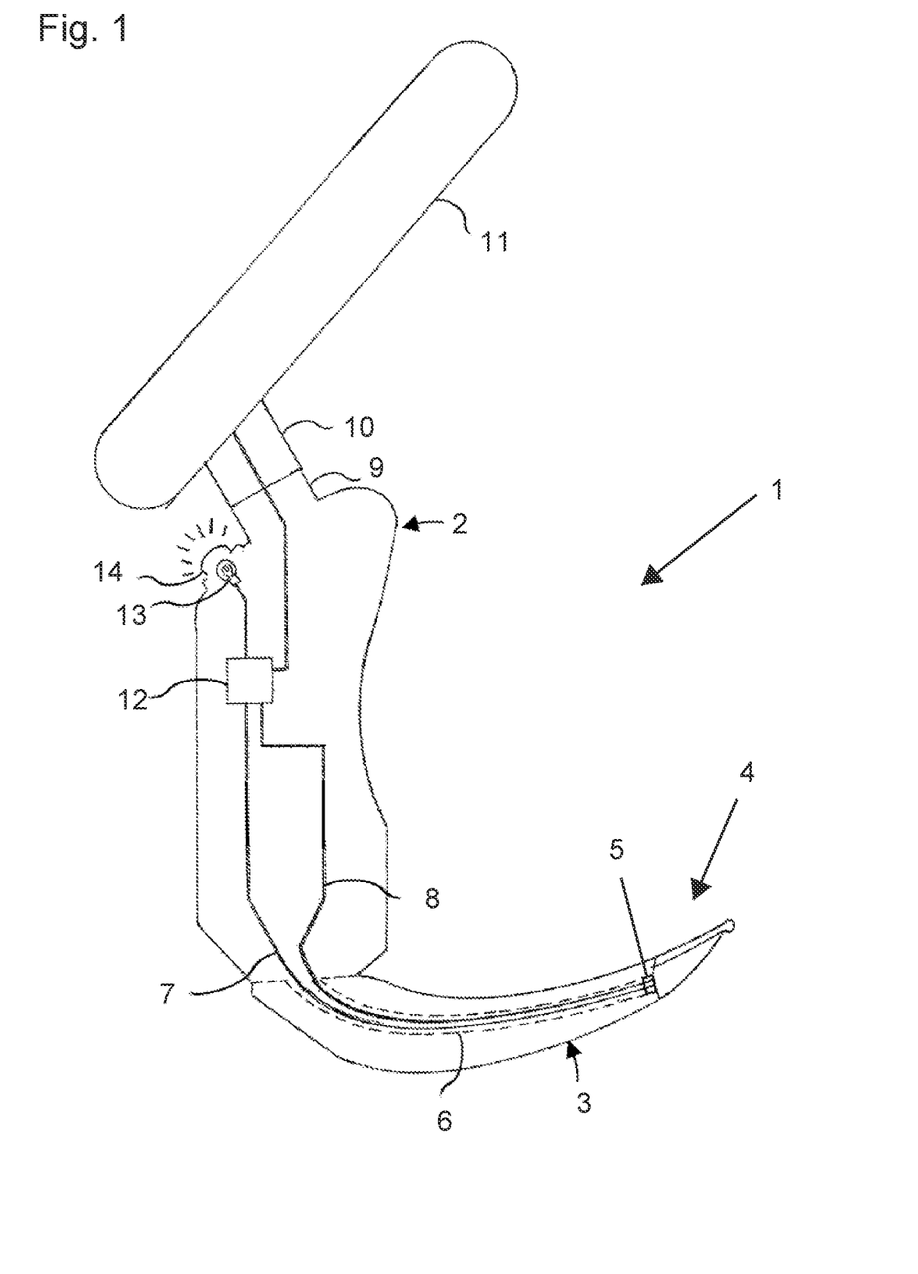
FIG. 1 shows an illustrative embodiment of an optical instrument in the form of a video laryngoscope.

In the present illustrative embodiment, the optical instrument shown in FIG. 1 is a video laryngoscope 1 having a handle 2 and having a blade 3 secured to the latter. As has been described above, the blade 3 is inserted into the patient's mouth in order to view the larynx during intubation. For this purpose, an electronics module 5 is integrated in a distal portion 4 of the blade 3, which electronics module 5 has an objective and an image sensor and also an LED for illumination (not shown). The objective and illumination means are oriented distally toward the end of the blade 3. Electrical signal lines 7 and 8 run in a channel 6 in the blade 3 and connect the electronics module 5 to a controller 12 and to a coupling site 9 at the handle, which coupling site 9 is connected to a monitor 11 via a plug 10. The controller 12 controls image processing and illumination and also a signal light 13, which serves as a status indicator 14 and shows the user the operating state of the laryngoscope 1.

The frontmost lens of the objective or a cover glass can be held, as is described here, in a mount in the blade 3, such that an edge of the mount protrudes distally and, in at least one portion, is caulked such that the non-caulked portion forms a stray-light protection between the frontmost lens and the LED.

Figure 2:
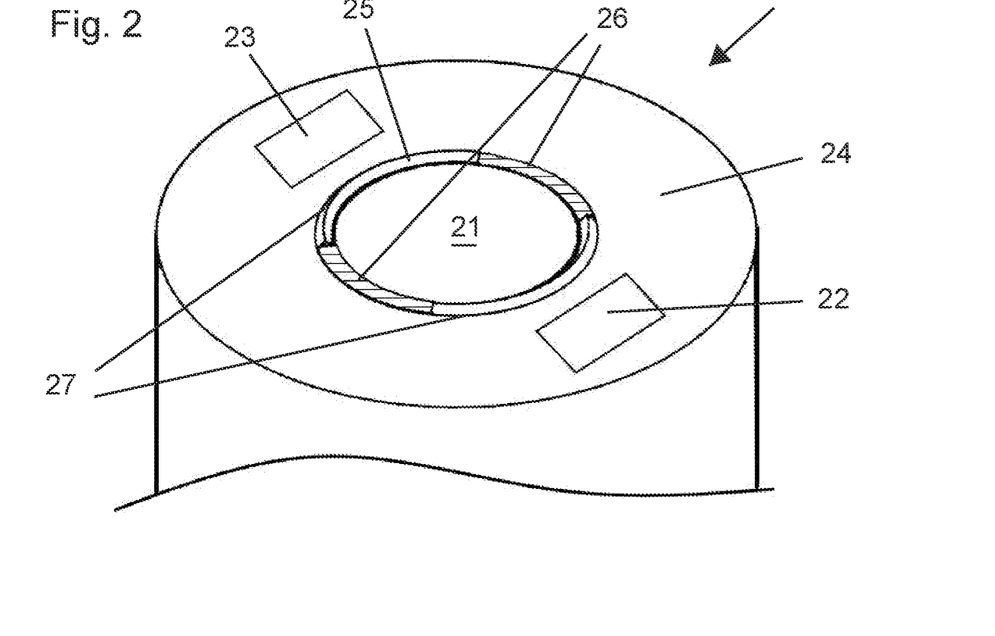
FIG. 2 shows an illustrative embodiment of a distal end of an endoscope.

FIG. 2 shows the distal end of an example of an endoscope 20. The latter has an optical system with a cover glass 21 and two LEDs 22 and 23, which are together arranged in a distal end face 24 of the endoscope 20. The LEDs 22 and 23 are mounted laterally, and opposite each other, next to the cover glass 21, such that an observed region is uniformly illuminated by the LEDs. The light-emitting face is in each case equivalent to the face of the LED. The optical system and cover glass 21 are held in a mount 25, for example adhesively bonded into the latter. The mount 25 is in turn mounted in the body of the endoscope 20. The distal end of the mount 25 forms an edge reaching beyond the distal end face 24, with two reshaped edge portions 26 and two non-reshaped edge portions 27. The distal direction is here toward the top in the figure. The reshaped portions 26, here shown with hatching, are caulked and hold the cover glass 21 in the distal direction with form-fit engagement in the mount 25. The distal edge of the mount 25 has been caulked such that the non-caulked portions 27 each lie between the cover glass 21 and one of the LEDs 22 and 23. In this way, the cover glass 21 and, behind it, the optical system of the instrument 20 are protected from illumination light and stray light from the LEDs 22 and 23. As can be seen from FIG. 2, the edge is small or low in the distal direction compared to the diameter of the mount 25 and of the cover glass 21. Only a little additional material has to be provided on the mount in order to form the distal edge and to secure the optical element by the mount also in the distal direction with form-fit engagement.

Various embodiments of an optical instrument are set out schematically below. As has been described above, the instrument can be an endoscope, but likewise a laryngoscope, an exoscope or another optical instrument as used in medicine.

Figure 3:
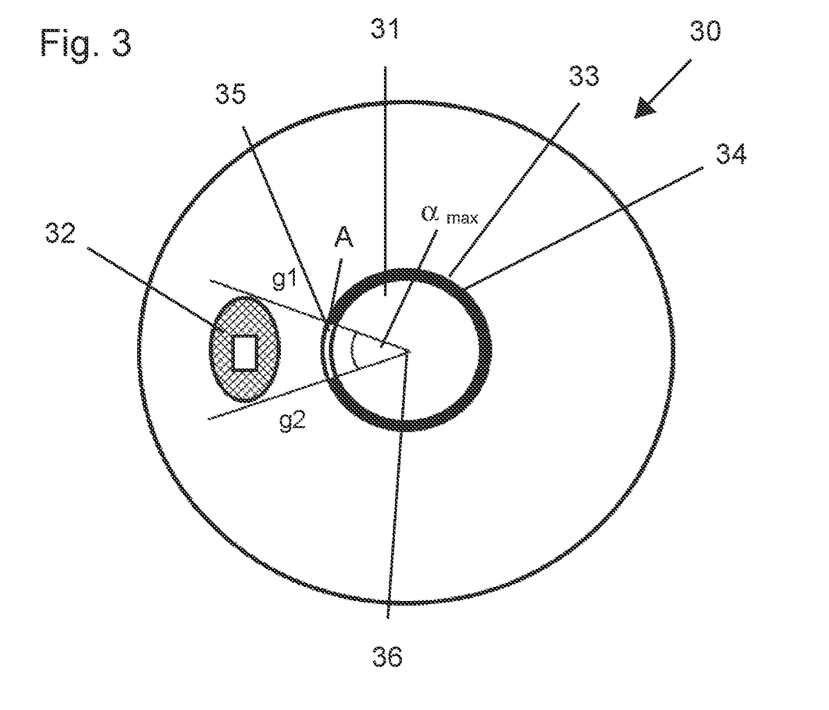
FIG. 3 shows a schematic view of an example of an instrument with an illumination unit, seen from the distal direction.

FIG. 3 first of all shows an instrument with an instrument body 30, a cover glass 31 and an individual LED, seen from the distal direction. The LED is arranged in a depression in the end face of the instrument body 30 alongside the cover glass 31 and is sealed there behind a glass window with a transparent adhesive. The adhesive scatters the emerging light of the LED in such a way that the entire sealed surface illuminates during operation. Therefore, reference is made in the present case to a light-emitting face 32, which can be identical to the face of the illumination means itself, but, as has been described above, can also reach beyond this. The light-emitting face 32 is shown here with cross-hatching and illuminates similarly to the LED shown by the rectangle in the cross-hatched surface. The cover glass 31 is in turn held in a mount 33, for example adhesively bonded thereto. The mount 33 has a distally protruding edge which has been caulked in an edge portion 34, here shown in a dark color. This caulked portion 34 comprises a large part of the circumference of the mount 33. The non-caulked portion 35 of the edge of the mount, here shown in a light color, lies between the surface of the cover glass 31 and the light-emitting face 32. If one considers the here acute angle enclosed by two imaginary straight lines g1 and g2 which start from the center point 36 of the cover glass 31 and intersect or touch the light-emitting face 32, this angle is maximal when the straight lines enclose the illumination face 32 and touch the outermost boundaries of this surface. The part A of the circumference of the distal edge of the mount 33 that has not been reshaped, and that forms the non-caulked portion 35, lies in the region of this angle $\alpha_{max}$. In this way, a stray-light protection is defined which in particular keeps the central part of the optical system free from stray light. If the light-emitting face 32 is larger than shown here, for example if it partially surrounds the cover glass 31, the angle $\alpha_{max}$ can of course also be considerably larger and the non-caulked portion 35 can refer to a larger part A than shown here. This will depend on the size and arrangement of the light-emitting face 32.

Figure 4:
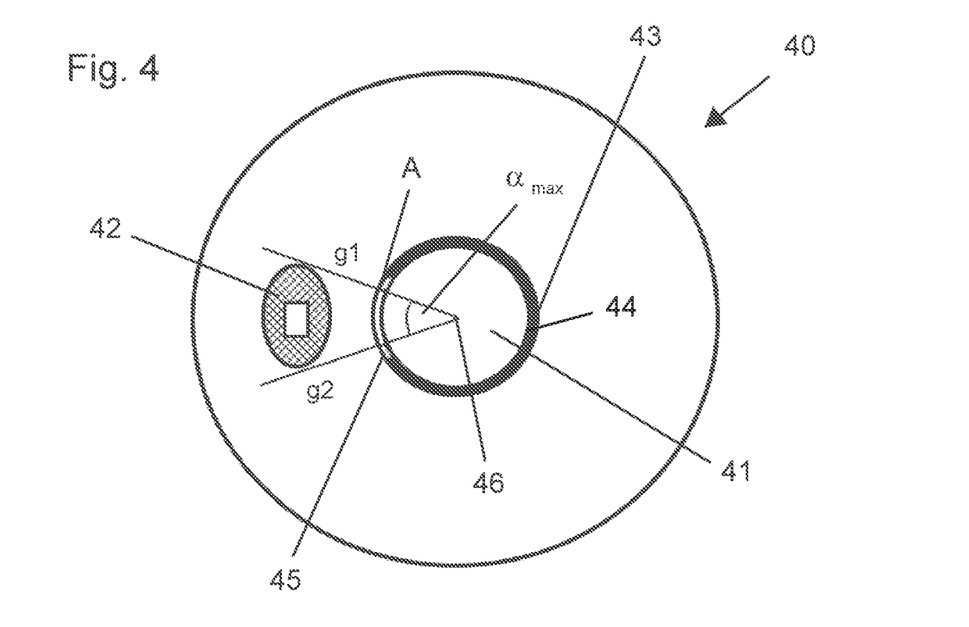
FIG. 4 shows a schematic view of a further example of an instrument with an illumination unit, seen from the distal direction.

The part A can be regarded as a minimum portion of the mount that is not reshaped in order to form the stray-light protection. FIG. 4 shows that the non-reshaped part can also be larger than the part A defined here. The figure again shows a distal front end of a medical instrument body 40, with a cover glass or a front lens 41, an illumination unit in the form of an LED with a light-emitting face 42, shown with cross-hatching as before, and a mount 43 in which the cover glass or the front lens 41 is fitted. The mount 43 is arranged in the instrument body 40. Once again, in the same way as for FIG. 3, an angle $\alpha_{max}$ is defined by imaginary straight lines g1 and g2 which start from the center point 46 of the cover glass or of the front lens 41. As can be seen, the non-caulked edge portion 45 on the circumference of the mount 43 is here larger than the part A that is enclosed by the angle $\alpha_{max}$. In this embodiment, the non-caulked portion 45, here shown in a light color, between cover glass 41 and light-emitting face 42 has been chosen in order to offer still better stray-light protection for the optical system of the instrument. The rest of the distal edge of the mount 43 has been caulked (shown in a dark color) in order to hold the cover glass 41 with form-fit engagement in the mount.

Figure 5:
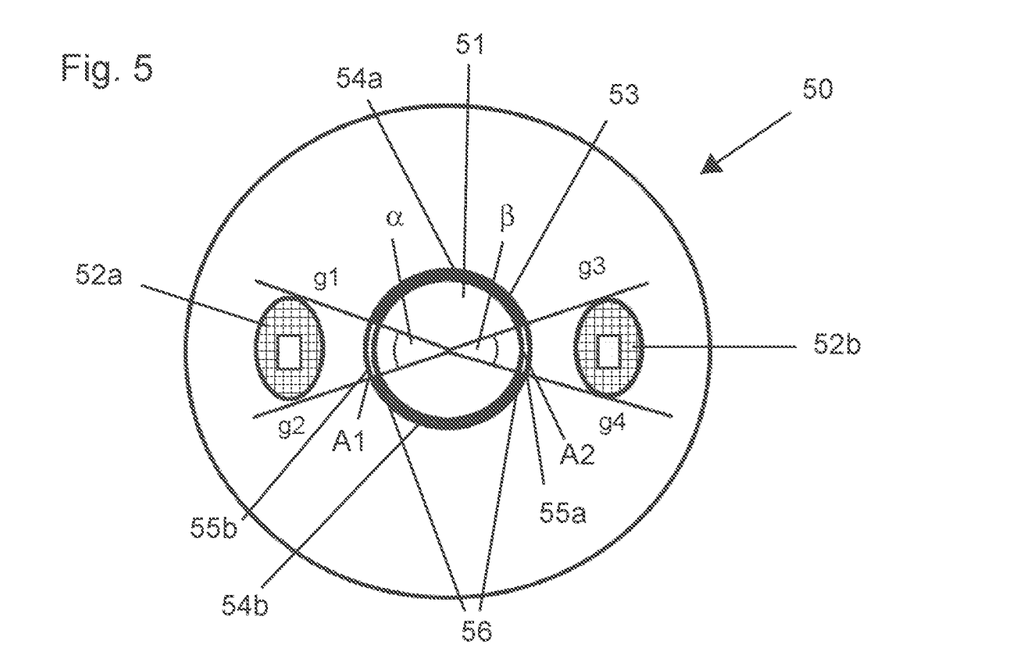
FIG. 5 shows a schematic view of an example of an instrument with two illumination units, seen from the distal direction.

In order to achieve more uniform illumination of the observed region in front of the instrument, two or more illumination units are often present on the instrument. It is then necessary for illumination light or stray light from the two illumination units to be kept away from the optical element. In the example shown in FIG. 5, two LEDs with light-emitting faces 52a and 52b (shown with cross-hatching) are arranged laterally, and opposite each other, alongside a front lens 51 of the instrument body 50. The front lens 51 is held by a mount 53 which is fitted, for example adhesively bonded, in the instrument body 50. The distally protruding distal edge of the mount 53 now has two reshaped, here caulked, portions 54a and 54b (shown in a dark color) and two non-caulked portions 55a and 55b (shown in a light color). The non-caulked portions are each arranged between the front lens 51 and the light-emitting faces 52a and 52b. As is shown in FIG. 3, the non-caulked portions 55a and 55b each lie in an angle range α and β, respectively, which are defined by the straight lines g1 and g2 and, respectively, g3 and g4 starting from the center point 56 of the front lens 51. The portions 55a and 55b here correspond exactly to the parts A1 and A2, as are defined by the angles on the circumference of the mount 53. It is of course likewise conceivable that the non-caulked portions 55a and 55b are larger than A1 or A2, in order to screen the front lens 51 still more from the LEDs. The angles α and β are here shown as acute angles, but, with corresponding extension of the light-emitting faces 52a and 52b, they can also be greater than 90°. Depending on the design and arrangement of the illumination means, the angles and therefore the non-caulked portions of the mount 53 can also be of different sizes. In the present illustrative embodiment, all the other portions 54a and 54b of the distal edge of the mount 53 have been caulked, in order to hold the front lens 51 securely in the mount.

Figure 6:
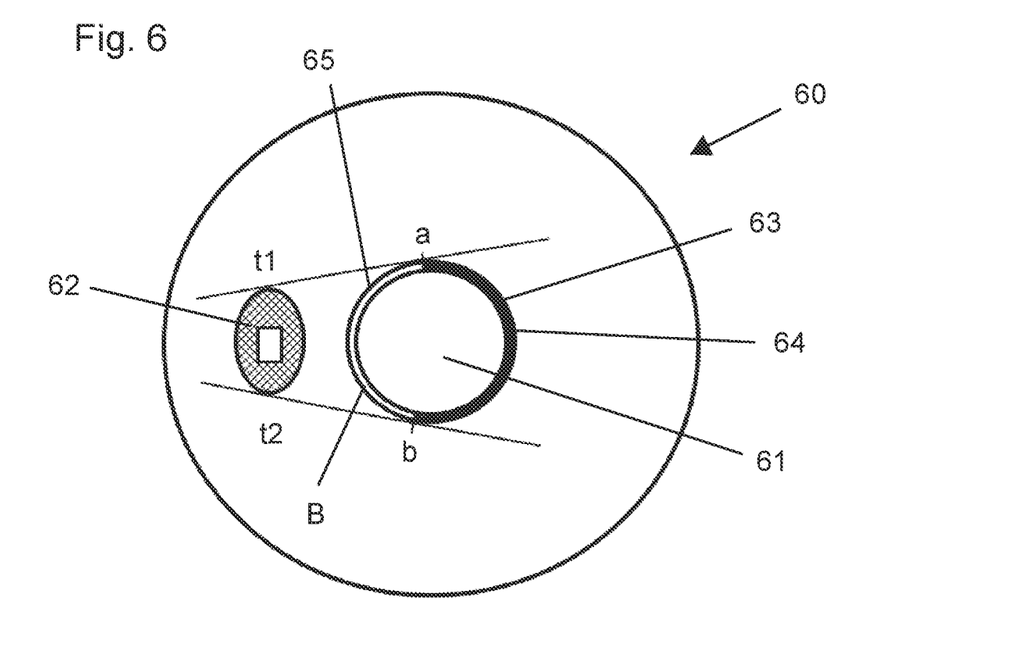
FIG. 6 shows a schematic view of a further example of an instrument with an illumination unit, seen from the distal direction.

In another illustrative embodiment, as shown in FIG. 6, a portion 64 (shown in a dark color) of a mount 63 arranged in the instrument body 60 has again been reshaped at its distal edge in order to hold a cover glass 61 in the mount 63. By contrast, a complementary portion 65 (shown in a light color) has not been reshaped and here comprises a part B of the circumference of the distal edge of the mount 63. This portion 65 lies between the cover glass 61 and an LED having a surrounding illuminating surface 62 (shown with cross-hatching) which is arranged alongside the cover glass 61. The part B is formed by a part of the distal edge that lies between two points a and b, where two tangents t1 and t2 to the mount edge intersect or touch, in their continuation, the outermost dimensions of the light-emitting face 62. Part B is the portion of maximum length for which this is still the case. Portion 65 here comprises precisely the part B, although it is also equally conceivable that the non-reshaped portion is larger than B and offers still more protection against stray light entering the optical system.

This embodiment too can be configured with two or more illumination units, as has been described above. Particularly preferably, a non-reshaped portion of the distal edge of the mount comprises a part of the circumference of the mount that is greater than or equal to the previously defined part A and smaller than or equal to the previously defined part B. The exact selection of the portion will be made, by a person skilled in the art, depending on the position and size of the illumination units and on other circumstances of the instrument.

Figure 7:
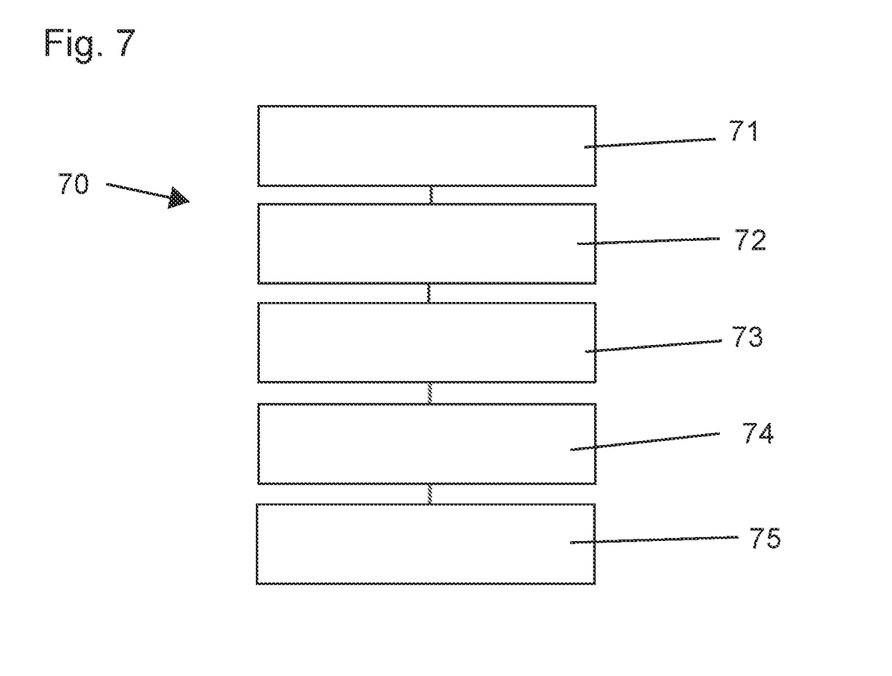
FIG. 7 shows a method for producing an optical instrument.

A method for producing an optical instrument described here is shown in FIG. 7. It comprises the following steps:
providing 71 an instrument body, for example an endoscope, laryngoscope, exoscope or microscope,
arranging 72, in the instrument body, at least one optical element for receiving light from a region outside the instrument body and at least one illumination unit for illuminating this region, for example a front lens and a LED, arranging 73 the optical element in a mount, such that the mount extends in the distal direction beyond the optical element and there forms a distal edge, for example adhesively bonding the front lens into the mount, fastening 74 the mount in the instrument body, for example adhesively bonding the mount into a blade part of a laryngoscope, reshaping 75 the distal edge in at least one portion, such that the reshaped portion of the distal edge holds the optical element, for example the front lens, in the distal direction with form-fit engagement, and the at least one non-reshaped portion of the distal edge is arranged such that it forms a stray-light protection by which illumination light coming from the illumination unit is kept away from the optical element. The reshaping is effected preferably by caulking the distal edge using a stamping tool, as is known to a person skilled in the art.

The same considerations as before apply here, and the aforementioned illustrative embodiments can be produced by the method 70.

Figure 8:
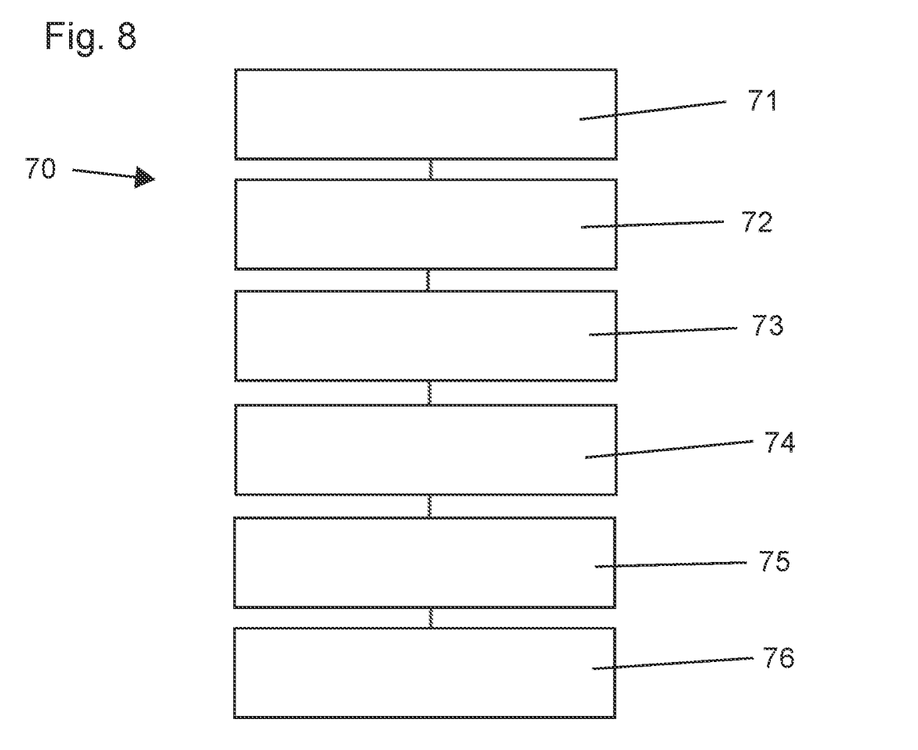
FIG. 8 shows the method from FIG. 7, with a further step.

In a further variant of the method 70, shown in FIG. 8, the method further comprises a step 76 of arranging at least a second illumination unit in the instrument body and reshaping a second, separate portion of the distal edge, such that the non-reshaped portions of the distal edge keep illumination light, coming from the two illumination units, away from the optical element.

This method can also be carried out in the manner described above and can produce the stated and further embodiments with two or more illumination units. In particular, here, as also in the embodiment with only one illumination unit, the reshaping of the distal edge is effected by caulking using a stamping tool, wherein the instrument body is clamped in a retainer and the distal edge of the in particular metallic mount is deformed by a pressure applied by the stamping tool. For example, the protruding distal edge is pressed flat by the caulking, such that with its new width it protrudes past the optical element and thus secures the latter in the mount. In addition, the stamping tool can be designed in such a way that the flat caulked edge is formed with a bevel to the outside. In this way, it is possible to ensure the possibility of good cleaning.

An optical instrument as described here was produced in particular by the method likewise described here.

LIST OF REFERENCE SIGNS 1 laryngoscope
2 handle
3 blade
4 distal portion
5 electronics module
6 channel
7 electrical signal line
8 electrical signal line
9 coupling site
10 plug
11 monitor
12 controller
13 signal light
14 status indicator
20 endoscope body
21 cover glass
22 LED
23 LED
24 distal end face
25 mount
26 caulked edge portions
27 non-caulked edge portions
30 instrument body
31 cover glass
32 light-emitting face
33 mount
34 caulked edge portion
35 non-caulked edge portion
36 center point of the cover glass
g1, g2 straight lines
40 instrument body
41 cover glass
42 light-emitting face
43 mount
44 caulked edge portion
45 non-caulked edge portion
46 center point of the cover glass
g1, g2 straight lines
50 instrument body
51 front lens
52a/b light-emitting faces
53 mount
54a/b caulked portions
55a/b non-caulked portions
56 center point of the front lens
g1, g2, g3, g4 straight lines
60 instrument body
61 cover glass
62 light-emitting face
63 mount
64 caulked portion
65 non-caulked portion
a, b contact points of the tangent
t1, t2 tangents
70 production method
71 providing step
72 arranging step
73 further arranging step
74 fastening step
75 reshaping step
76 further arranging and reshaping step

The invention claimed is:

1. An optical instrument configured for viewing a living thing for medical purposes, comprising:
an instrument body,
wherein the instrument body accommodates at least one optical element configured to receive light from a region outside the instrument body and at least two illumination units configured to illuminate this region,
wherein the optical element is held in the instrument by a mount which extends in the distal direction beyond the optical element and there forms a distal edge,
wherein the distal edge is reshaped in at least two separate portions, such that the reshaped portions of the distal edge hold the optical element in the distal direction with form-fit engagement,
wherein at least one non-reshaped portion of the distal edge is arranged such that it forms a stray-light protection, by which illumination light coming from the at least two illumination units are kept away from the optical element.

2. The optical instrument according to claim 1, wherein the mount is made of metal.

3. The optical instrument according to claim 2, wherein the at least one reshaped portion has been reshaped mechanically by caulking.

4. The optical instrument according to claim 1, wherein the height of the distal edge of the non-reshaped portion measures at least 0.5% and at most 5% of the circumference of the distal edge.

5. The optical instrument according to claim 1, wherein at least one illumination unit has a light-emitting face, and the at least one non-reshaped portion is arranged between the optical element and the light-emitting face.

6. The optical instrument according to claim 1, wherein the instrument is a laryngoscope with a handle and with a blade, wherein the optical element and the illumination unit are arranged at the blade.

7. A method to produce an optical instrument configured to view a living thing for medical purposes, comprising:
- providing an instrument body,
- arranging, in the instrument body, at least one optical element configured to receive light from a region outside the instrument body and at least one illumination unit configured to illuminate this region,
- arranging the optical element in a mount, such that the mount extends in the distal direction beyond the optical element and there forms a distal edge,
- fastening the mount in the instrument body,
- reshaping the distal edge in at least one portion, such that the reshaped portion of the distal edge holds the optical element in the distal direction with form-fit engagement, and the at least one non-reshaped portion of the distal edge is arranged such that it forms a stray-light protection by which illumination light coming from the illumination unit is kept away from the optical element, and
- arranging at least a second illumination unit in the instrument body and reshaping a second, separate portion of the distal edge, such that the at least one non-reshaped portion of the distal edge keeps illumination light, coming from the two illumination units, away from the optical element.

8. The method according to claim 7, wherein the reshaping of the distal edge in the at least one portion is carried out by caulking the distal edge.

* * * * *